United States Patent
Lipton et al.

(10) Patent No.: US 11,434,501 B2
(45) Date of Patent: Sep. 6, 2022

(54) SPRR1A AS A GENETIC TARGET FOR TREATING NEURODEGENERATIVE DISEASES

(71) Applicant: Board of Trustees of Michigan State University, East Lansing, MI (US)

(72) Inventors: Jack W. Lipton, Grand Rapids, MI (US); Nicholas Kanaan, Grand Rapids, MI (US); Timothy Collier, Grand Rapids, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 123 days.

(21) Appl. No.: 15/507,569

(22) PCT Filed: Aug. 27, 2015

(86) PCT No.: PCT/US2015/047165
§ 371 (c)(1),
(2) Date: Feb. 28, 2017

(87) PCT Pub. No.: WO2016/033318
PCT Pub. Date: Mar. 3, 2016

(65) Prior Publication Data
US 2017/0283829 A1    Oct. 5, 2017

Related U.S. Application Data

(60) Provisional application No. 62/043,103, filed on Aug. 28, 2014.

(51) Int. Cl.
| | |
|---|---|
| *C12N 15/86* | (2006.01) |
| *A61K 49/14* | (2006.01) |
| *A61K 38/39* | (2006.01) |
| *A61K 48/00* | (2006.01) |
| *A61K 35/30* | (2015.01) |
| *A61K 38/04* | (2006.01) |
| *A61K 39/395* | (2006.01) |
| *G01N 33/50* | (2006.01) |
| *C12N 15/00* | (2006.01) |

(52) U.S. Cl.
CPC .............. *C12N 15/86* (2013.01); *A61K 35/30* (2013.01); *A61K 38/04* (2013.01); *A61K 38/39* (2013.01); *A61K 39/395* (2013.01); *A61K 48/005* (2013.01); *A61K 49/14* (2013.01); *G01N 33/5008* (2013.01); *C12N 15/00* (2013.01); *C12N 2750/14143* (2013.01); *G01N 2800/2835* (2013.01)

(58) Field of Classification Search
None
See application file for complete search history.

(56) References Cited

U.S. PATENT DOCUMENTS

| | | | | |
|---|---|---|---|---|
| 7,335,636 | B2 * | 2/2008 | Strittmatter | ........ A61K 38/1709 424/184.1 |
| 2005/0054094 | A1 | 3/2005 | Strittmatter et al. | |
| 2006/0127397 | A1 | 6/2006 | Strittmatter et al. | |
| 2013/0267464 | A1 | 10/2013 | Jorgensen et al. | |

FOREIGN PATENT DOCUMENTS

WO    2014053038    *   4/2014

OTHER PUBLICATIONS

Gardlik et al, Med Sci Monit 11: RA110-121, 2005.*
Burger et al. (Mol Ther 10: 302-317, 2004).*
Bonilla et al (J. Neurosci 22: 1303-1315, 2002).*
Huebner et al., (Res Probl Cell Differ 48: 339-351(1-13), 2009).*
Halliday et al. (Clin Exp Pharmacol Physiol 27: 1-8, 2000).*
Masrori et al (Eu J Neurol 27: 1918-1929, 2020).*
Feigin et al., (Curr Opin Neurol 15: 483-489, 2002).*
Meili et al. "Dorsal Root Ganglia Sensory Neuronal Cultures: a tool for drug discovery for peripheral neuropathies," Expert *Opin Drug Discov.* 4(10):1035-1045 (2009).
Starkey et al., "Expression of the regeneration-associated protein SPRR1A in primary sensory neurons and spinal cord of the adult mouse following peripheral and central injury," *J Comp Neurol.* 513(1):51-68 (2009).
International Report on Patentability PCT/US2015/047165 dated Dec. 7, 2015.
International Search Report PCT/US2015/047165 dated Oct. 8, 2015.

* cited by examiner

*Primary Examiner* — Daniel E Kolker
*Assistant Examiner* — Aditi Dutt
(74) *Attorney, Agent, or Firm* — Foley Hoag LLP

(57) ABSTRACT

This invention relates to the prevention and treatment of neurodegenerative diseases by administering compositions that increase the activity of a small proline-rich repeat 1 A protein (Sprr1A), or derivative thereof to the brain. Specifically, the compositions may comprise a nucleic acid molecule encoding a Sprr1A protein or a biologically-active portion thereof. The neurodegenerative disease may be Parkinson's Disease, Alzheimer's disease, amyotrophic lateral sclerosis, or traumatic brain injury.

14 Claims, 4 Drawing Sheets
Specification includes a Sequence Listing.

Figure 4
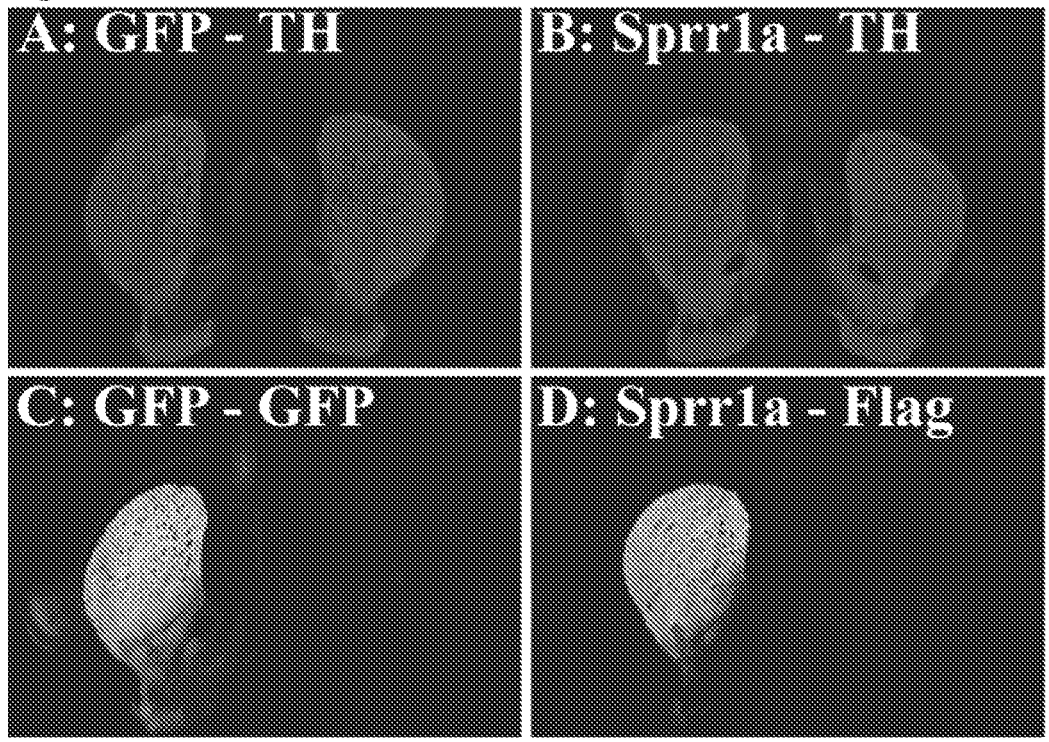
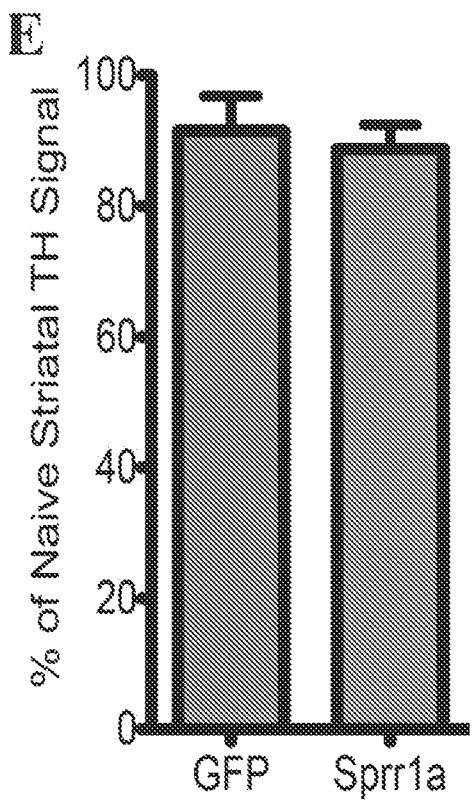

SPRR1A AS A GENETIC TARGET FOR TREATING NEURODEGENERATIVE DISEASES

PRIORITY CLAIM

This application is a 371 National Stage Application of PCT/US2015/047165, filed Aug. 27, 2015, which claims the benefit of priority to U.S. Provisional Patent Application No. 62/043,103 filed on Aug. 28, 2014, hereby incorporated by reference in their entirety.

GOVERNMENT INTEREST

This invention was made with government support under NS058830 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 17, 2015, is named MSS_00425_SL.txt and is 4,663 bytes in size.

BACKGROUND

Neurodegenerative diseases are characterized by a progressive neurodegenerative process in which neuron structure and/or function are lost over time. Among the most common and most severe neurodegenerative diseases are amyotrophic lateral sclerosis, Alzheimer's disease. Huntington's disease, and Parkinson's Disease. Though genetic characteristics have been linked to some neurodegenerative diseases, the precise causes of most neurodegenerative diseases remain unclear. Further, effective treatments remain elusive for nearly all forms of neurodegenerative disease.

Parkinson's Disease results from the death of dopamine-producing cells in the brain. Multiple studies suggest that Parkinson's Disease is a dying-back axonopathy, and thus, axonal degeneration may be a critical early event in Parkinson's Disease pathogenesis. A recent study demonstrated that patients lose their striatal dopamine projections early in the disease, well before significant somatic loss occurs. This observation may explain why dopamine somatic preservation strategies have not been successful in clinical trials: these strategies do not prevent the dying-back of axonal dopamine projections.

BRIEF DESCRIPTION OF THE FIGURES

FIG. 2 shows that Sprr1a provides significant axonal and synaptic protection against 6-OHDA-induced degeneration in rats. Licor densitometry of TH staining (indicator of dopamine axons) in the striatum of animals treated with rAAV-GFP (A) or rAAV-Sprr1a (B) for 1 month prior to striatal 6-OHDA administration. Significantly more TH signal remains in rAAV-Sprr1a treated animals compared to rAAV-GFP animals (G). Licor images of striatal GFP (C) and Sprr1a (D) confirm expression of the rAAV transgenes. Licor densitometry of synaptophysin (a synaptic marker) in the striatum of animals treated with rAAV-GFP (E) or rAAV-Sprr1a (F). Significantly synaptic loss is seen in rAAV-GFP treated animals compared to rAAV-Sprr1a animals (H). *p<0.05 in an unpaired t-test.

FIG. 3 indicates that striatal DA fiber denervation is reduced by Sprr1a overexpression prior to a 6-OHDA striatal lesion. As an indication of axoprotection, stereological volume measurements of lesioned (A and C) striatal regions that appeared unaltered (light gray border; left encircled area in panel C, i.e. similar to intact striata B and D), intermediately denervated (white borders; upper left encircled area in panel A; upper right encircled area in panel C) or severely denervated (dark gray borders; lower right encircled area in panel A; small, encircled area in panel C) after 6-OHDA administration. The severely denervated region was significantly reduced in rAAV-Sprr1a treated animals (C) compared to those receiving rAAV-GFP (A), and in Sprr1a animals ~9% of the striatum appeared "normal" compared to 0% in GFP animals (E). Striatal TH axon length was quantified using stereological methods. Pretreatment with rAAV-Sprr1a preserved significantly more dopamine axons compared to the rAAV-GFP (F). SN DA neuron counts indicate that significant cell loss has not occurred at this time point (G; A-D insets). *p<0.05 in a two-way repeated measures ANOVA with Bonferonni post-hoc test.

FIG. 4 consists of five panels, labelled panels A-E. FIG. 4 demonstrates that overexpression of Sprr1a in the nigrostriatal system is safe. rAAV-Sprr1a and GFP were expressed in the intact nigrostriatal system and 3 weeks later the animals were collected. Neither GFP (A and C) nor Sprr1a (B and D) overexpression significantly changed the level of TH in the striatum (E).

SUMMARY

Figure 1:
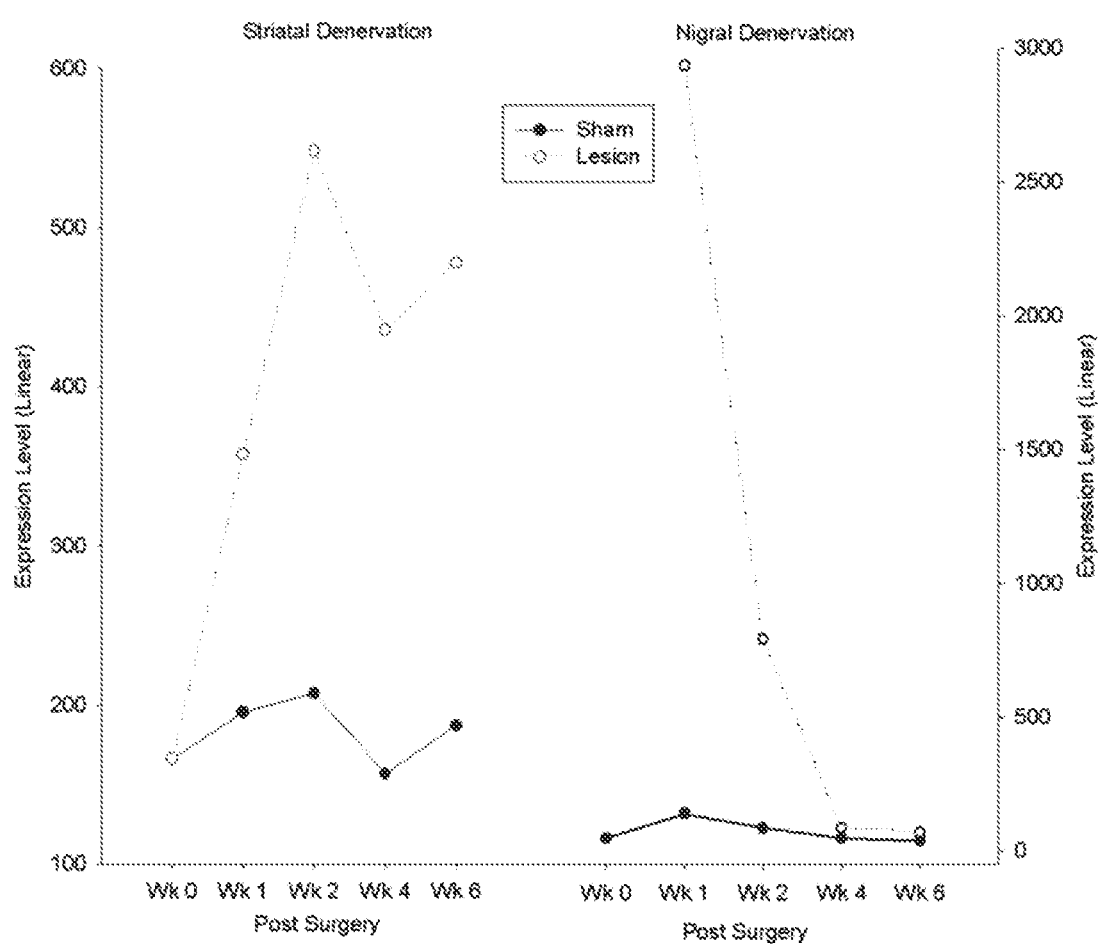
FIG. 1 depicts the expression level of Sprr1A in the nigra and striata of rats in response to 6-hydroxydopamine-induced cell loss.

In some aspects, the invention relates to methods for treating a neurodegenerative disease in a subject in need thereof, comprising administering to the subject a therapeutically effective amount of a composition, wherein said composition increases the activity of a small proline-rich repeat 1a protein ("Sprr1A"). The neurodegenerative disease may be Parkinson's Disease, Alzheimer's disease, amyotrophic lateral sclerosis, or traumatic brain injury. In some embodiments, the neurodegenerative disease is Parkinson's Disease.

The composition may comprise a nucleic acid molecule. The nucleic acid molecule may encode a Sprr1A protein or a biologically-active portion thereof.

The composition may comprise a virus. The virus may be an adeno-associated virus ("AAV"), adenovirus, herpes simplex virus, or lentivirus. In some embodiments, the virus is AAV, such as AAV1. The genome of the virus may comprise the nucleic acid molecule.

In certain embodiments, the genome of the virus comprises the nucleic acid molecule. The nucleic acid molecule may comprise a nucleotide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with at least 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, or 266 consecutive nucleotides selected from the nucleotide sequence set forth in SEQ ID NO: 1, 3, 4, or 5. For example, in some embodiments, the nucleic acid molecule comprises a nucleotide sequence that has at least 80% sequence homology with at least 36 consecutive nucleotides selected from the nucleotide sequence set forth in SEQ ID NO: 1. In other embodiments, the nucleic acid molecule comprises a nucleotide sequence that has at least 95% sequence homology with at least 36 consecutive nucleotides selected from the nucleotide sequence set forth in SEQ ID NO: 1. Still, in other embodiments, the nucleic acid molecule comprises at least 36 consecutive nucleotides selected from the nucleotide sequence set forth in SEQ ID NO: 1. Alternatively, the nucleic acid molecule may comprise a nucleotide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the nucleotide sequence set forth in SEQ ID NO: 1, 3, 4, or 5.

The nucleic acid molecule may encode an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41.42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 consecutive amino acids selected from the amino acid sequence set forth in SEQ ID NO:2. For example, in some embodiments, the nucleic acid molecule may encode an amino acid sequence that has at least 80% sequence homology with at least 12 consecutive amino acids selected from the amino acid sequence set forth in SEQ ID NO:2. In other embodiments, the nucleic acid molecule encodes an amino acid sequence that has at least 95% sequence homology with at least 12 consecutive amino acids selected from the amino acid sequence set forth in SEQ ID NO:2. Still, in other embodiments, the nucleic acid molecule encodes at least 12 consecutive amino acids selected from the amino acid sequence set forth in SEQ ID NO:2. Alternatively, the nucleic acid molecule may encode an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the amino acid sequence set forth in SEQ ID NO:2.

In some embodiments, administering the composition comprises inserting the composition at a desired location. The desired location may be the brain. In some embodiments, the desired location is the substantia nigra, nigrostriatal system, hippocampus, medial temporal lobe, cerebral cortex, or spinal cord. Inserting may comprise injecting the composition.

In some embodiments, the subject is a mammal. For example, the subject may be a primate, porcine, canine, ovine, or rodent. In certain embodiments, the subject is a human.

In some aspects, the invention relates to a method for treating Parkinson's Disease in a subject in need thereof, comprising administering to the subject a therapeutically effective amount of a composition, wherein (i) the composition comprises a nucleic acid molecule; (ii) the nucleic acid molecule encodes a small proline-rich repeat 1a protein ("Sprr1A"), or a biologically-active portion thereof; (iii) and administering comprises inserting the composition into the brain.

DEFINITIONS

The articles "a" and "an" are used herein to refer to one or to more than one (i.e., to at least one) of the grammatical object of the article. By way of example, "an element" means one element or more than one element.

The term "activity" refers to the total capacity of a cell to perform a function. A treatment that increases the activity of a Sprr1A protein in a cell may increase the amount of Sprr1A in a cell or increase the efficiency of Sprr1. For example, Sprr1A gene therapy increases the amount of Sprr1A in the cell. Additionally, changes to the SPRR1A gene may increase its activity; for example, a mutation to the SPRR1A gene that truncates its Sprr1A protein product may increase Sprr1A activity in a cell.

As used herein, the term "administering" means providing a pharmaceutical agent or composition to a subject, and includes, but is not limited to, administering by a medical professional.

The term "biologically-active portion" refers to an amino acid sequence that is less than a full-length amino acid sequence, but exhibits at least one activity of the full length sequence. For example, a biologically-active portion of Sprr1A may refer to one or more domains of Sprr1A that has a neuroprotective effect. Such biologically-active portions of Sprr1A are known in the art (See. e.g., U.S. Pat. No. 7,335,636, incorporated by reference). Biologically-active portions of Sprr1A include peptides or polypeptides comprising amino acid sequences sufficiently identical to or derived from the amino acid sequence of the Sprr1A protein, e.g., the amino acid sequence as set forth in SEQ ID NO:2, which include fewer amino acids than the full length Sprr1A, and exhibit at least one activity of a Sprr1A protein. Typically, biologically active portions comprise a domain or motif having a neuroprotective effect. A biologically active portion of a Sprr1A protein can be a polypeptide which is, for example, 24 amino acids in length.

The term "encode" refers to nucleic acids that comprise a coding region, portion of a coding region, or compliments thereof. Both DNA and RNA may encode a gene.

The term "expression" refers to the amount of a nucleic acid or protein (e.g., peptide, polypeptide, etc.) in a cell. The expression of either a nucleic acid or a protein may be increased or decreased. Increased expression of a protein refers to the increased translation of that protein. For example, inserting an additional copy of a gene encoding Sprr1A into a cell may increase the expression of Sprr1A mRNA and the Sprr1A polypeptide by providing an additional DNA template for transcription.

The term "gene," as used herein, encompasses nucleotide sequences that encode amino acid sequences, including nucleotide sequences that did not derive from a genomic sequence. The term also includes nucleotide sequences that are upstream or downstream of the coding sequence, such as regulatory regions, and it includes intron sequences.

The terms "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: antisense nucleic acid molecules, small interfering RNA molecules, short hairpin RNA molecules, microRNA molecules, coding or non-coding regions of genes or gene fragments, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body.

The term "regulatory region" refers to nucleotide sequences that affect the transcription or translation of a gene but do not encode an amino acid sequence. Regulatory regions include promoters, operators, enhancers, and silencers.

An oligonucleotide "specifically hybridizes" to a target polynucleotide if the oligomer hybridizes to the target under physiological conditions, with a Tm substantially greater than 45° C., or at least 50° C., or at least 60° C.-80° C. or higher. Such hybridization corresponds to stringent hybridization conditions. At a given ionic strength and pH, the Tm is the temperature at which 50% of a target sequence hybridizes to a complementary polynucleotide. Hybridization may occur with "near" or "substantial" complementarity of the antisense oligomer to the target sequence, as well as with exact complementarity.

As used herein, the term "subject" means a human or non-human animal selected for treatment or therapy. Subjects may include mammals, such as primates, porcine, canine, ovine, and rodentia.

The term "Sprr1A" refers to small proline-rich repeat 1a protein, homologs (e.g., small proline-rich repeat 1a protein-like proteins), orthologs (e.g., human, mouse, rat sequences), as well as portions of Sprr1A proteins, homologs, and orthologs that are therapeutically effective. One skilled in the art can readily identify portions of Sprr1A that are therapeutically effective. For example, U.S. Pat. No. 7,335,636 (incorporated by reference) identifies a 24-amino acid long peptide derived from mouse Sprr1A that increases axon growth. Thus, Sprr1A may refer to polypeptide sequences that are, for example, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, or 144 amino acids long. Sprr1A proteins are encoded by the SPRR1A gene.

The phrases "therapeutically-effective amount" and "effective amount" as used herein means the amount of a composition that is effective for producing the desired therapeutic effect in at least a sub-population of cells in a subject at a reasonable benefit/risk ratio applicable to any medical treatment.

"Treating" a disease in a subject or "treating" a subject refers to subjecting the subject to a pharmaceutical treatment, e.g., the administration of a drug, such that at least one symptom of the disease is decreased or prevented from worsening. The term "treating" includes prophylactic and therapeutic treatments. The terms prophylactic and therapeutic are art-recognized and include the administration of one or more compositions to a subject. If the composition is administered prior to a clinical manifestation of an unwanted symptom or condition (e.g., before a subject develops one or more symptoms of Parkinson's Disease) then the treatment is prophylactic (i.e., it protects the subject against developing the unwanted symptom or condition), whereas if the composition is administered after manifestation of the unwanted condition (e.g., after a subject develops Parkinson's Disease), the treatment is therapeutic, (i.e., it is intended to diminish, ameliorate, or stabilize the existing unwanted condition or side effects thereof). Thus, treating relates to the administration of a composition, such that at least one symptom of a condition is decreased or prevented from worsening in a subject or group of subjects relative to a subject or group of subjects who did not receive the composition; and treating also relates to the administration of a composition, such that the risk that a symptom will develop or worsen is diminished in a subject or group of subjects relative to a subject or group of subjects who did not receive the composition.

The term "vector" refers to the means by which a nucleic acid can be propagated and/or transferred between organisms, cells, or cellular components. Vectors include plasmids, linear DNA fragments, viruses, bacteriophage, pro-viruses, phagemids, transposons, and artificial chromosomes, and the like, that may or may not be able to replicate autonomously or integrate into a chromosome of a host cell. Additionally, the term vector refers to exogenous nucleotide sequences from plasmids, linear DNA fragments, viruses, bacteriophage, pro-viruses, phagemids, transposons, and artificial chromosomes, and the like, that have integrated into an organism's genome.

A. Sprr1A Sequences

Sprr1A protects neurons from axonal degeneration, which is a critical component of the degenerative process of dopamine neurons. Sprr1A is upregulated in the brains of rat Parkinson's models (FIG. 1; Example 1). Further, Sprr1A facilitates axonal regeneration and reduces the damage that ensues from neuron insults (Example 2). Thus, increasing Sprr1A activity in the brains of subjects suffering from Parkinson's Disease can impede disease progression. Similarly, increasing Sprr1A activity can generally impede the progression of neurodegenerative diseases that cause axonal degeneration.

The term "Sprr1A," as used herein, refers to small proline-rich repeat 1a protein, homologs (e.g., small proline-rich repeat 1a protein-like proteins), and orthologs (e.g., human, mouse, rat sequences), as well as portions of Sprr1A proteins, homologs, and orthologs that are therapeutically effective. The term "SPRR1A" refers to genes that encode a Sprr1A protein.

The SPRR1A gene may comprise conservative substitutions, deletions, and/or insertions while still encoding the same amino acid sequence. For example, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions, or to substitute amino acids that affect the function of the Sprr1A protein product. Additionally, the Sprr1A nucleotide and amino acid sequences vary among different species. Thus, the SPRR1A gene may comprise a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the nucleotide sequence set forth in SEQ ID NO: 1, 3, 4, or 5. Similarly, the Sprr1A protein may comprise an amino acid sequence having at least 80%, 81%, 82%, 83%, 84%, 85%, 86%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence homology with the amino acid sequence set forth in SEQ ID NO:2.

One skilled in the art can readily identify portions of Sprr1A that are therapeutically effective. For example, U.S. Pat. No. 7,335,636 (incorporated by reference) identifies a 24-amino acid long peptide derived from mouse Sprr1A that increases axon growth. Thus, Sprr1A may refer to an amino acid sequence that is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, or 144 amino acids long. Similarly, the SPRR1A gene may refer to a nucleotide sequence that is 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 nucleotides long or longer.

Amino acid substitutions, deletions and/or insertions may readily be made using peptide synthetic techniques well known in the art, such as solid phase peptide synthesis and/or any other synthetic techniques, or by recombinant DNA manipulation. Methods for the manipulation of DNA sequences to produce substitution, insertion, or deletion variants of a protein are well known in the art (e.g., Green & Sambrook, *Molecular Cloning: A Laboratory Manual*, (4th ed., 2012)). For example, techniques for making substitution mutations at predetermined sites in DNA are well known to those skilled in the art and include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis or other site-directed mutagenesis protocols.

To determine the percent identity of two amino acid sequences or of two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences can be determined using the Needleman and Wunsch (J. Molecular Biology 48:444-453 (1970)) algorithm which has been incorporated into the GAP program in the GCG software package (available at www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0 U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, e.g., ClustalW, ClustalX, and Clustal Omega.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'-3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

B. Viral Vectors

1. Adeno-Associated Virus

The nucleic acids of the invention can be delivered to the cells of the central nervous system by using an adeno-associated viral vector (AAV vector). The use of AAV vectors to deliver genes into the brain is well known in the art (See. e.g., U.S. Pat. Nos. 8,198,257 and 7,534,613, U.S. patent application Ser. No. 13/881,956, each of which is incorporated by reference).

AAV vectors for delivering a SPRR1A gene to a neuron are known in the art (See U.S. Pat. No. 7,335,636, incorporated by reference). AAV vectors can be constructed using known techniques to provide at least the operatively linked components of control elements including a transcriptional initiation region, an exogenous nucleic acid molecule, a transcriptional termination region and at least one post-transcriptional regulatory sequence. The control elements are selected to be functional in the targeted cell. The resulting construct which contains the operatively linked components is flanked at the 5' and 3' region with functional AAV inverted terminal repeat sequences (ITRs).

The nucleotide sequences of AAV ITR regions are known. The ITR sequences for AAV-2 are described, for example, by Kotin et al., Human Gene Therapy, 5:793-01 (1994); Fields & Knipe, Fundamental Virology, "Parvoviridae and their Replication" (2d ed. 1986). The skilled artisan will appreciate that AAV ITR's can be modified using standard molecular biology techniques (e.g., Green & Sambrook, *Molecular Cloning: A Laboratory Manual*, (4th ed., 2012)). Accordingly, AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including but not limited to, AAV-1, AAV-2, AAV-3, AAV-4, AAV-5, AAVX7, and the like. Furthermore, the 5' and 3' ITRs, which flank a selected nucleotide sequence in an AAV expression vector, need not necessarily be identical or derived from the same AAV serotype or isolate, so long as the ITR's function as intended, i.e., to allow for excision and replication of the bounded nucleotide sequence of interest when AAV rep gene products are present in the cell.

The skilled artisan can appreciate that regulatory sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter (Boshart et al., Cell, 41:521-30 (1985)), herpes virus thymidine kinase promoter (McKnight et al. Cell, 37: 253-62 (1984)), β-actin promoters (e.g., the human β-actin promoter, Ng et al., Molecular Cell Biology, 5:2720-32(1985)), and colony stimulating factor-1 promoter (Ladner et al., EMBO J., 6:2693-98(1987)).

Alternatively, the regulatory sequences of the AAV vector can direct expression of the gene preferentially in a particular cell type, i.e., tissue-specific regulatory elements can be used. Non-limiting examples of tissue-specific promoters which can be used include, central nervous system (CNS) specific promoters such as, neuron-specific promoters (e.g., the neurofilament promoter; Byrne and Ruddle, Proceedings Nat'l Acad. Sci. USA, 86:5473-77 (1989)) and glial specific promoters (Morii et al., Biochemical & Biophysical Research Communications, 175:185-91 (1991)). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus striatum, cerebral cortex, or within the cortex, the occipital, temporal, parietal or frontal lobes), or a combination thereof may be selected. The promoter may be specific for particular cell types, such as neurons or glial cells in the CNS. If it is active in glial cells, it may be specific for astrocytes, oligodendrocytes, ependymal cells, Schwann cells, or microglia. If it is active in neurons, it may be specific for particular types of neurons, e.g., motor neurons, sensory neurons, or interneurons. Additionally, it may be specific for neurons with a specific phenotype, e.g., dopamine-producing neurons, sertonin-producing neurons, etc. Preferably, the promoter is specific for cells in particular regions of the brain, for example, the cortex, striatum, nigra, and hippocampus.

Suitable neuronal specific promoters include, but are not limited to, neuron specific enolase (NSE) (Olivia et al., Genomics, 10:157-65 (1991). GenBank Accession No: X51956), and human neurofilament light chain promoter (NEFL) (Rogaev et al., Human Molecular Genetics, 1:781 (1992), GenBank Accession No: L04147). Glial specific promoters include, but are not limited to, glial fibrillary acidic protein (GFAP) promoter (Morii et al., Biochemical & Biophysical Research Communications, 175:185-91 (1991), GenBank Accession No: M65210), S100 promoter (Morii et al., Biochemical & Biophysical Research Communications, 175:185-91 (1991), GenBank Accession No: M65210) and glutamine synthase promoter (Van den et al., Biochimica Biophysica Acta, 2:249-51(1991), GenBank Accession No: X59834). In a preferred embodiment, the gene is flanked upstream (i.e., 5') by the neuron specific enolase (NSE) promoter. In another preferred embodiment, the gene of interest is flanked upstream (i.e., 5') by the elongation factor 1 alpha (EF) promoter. Suitable phenotype-specific promoters include, but are not limited to, tyrosine hydroxylase promoter, dopamine beta-hydroxylase, acetylcholinesterase promoter, choline acetyltransferase promoter, dopamine receptor I and II promoters, dopamine transporter promoter, vesicular monoamine transporter promoter, neuopsin promoter, and vesicular acetylcholine transporter promoter.

The AAV vector harboring the nucleotide sequence of interest, e.g., the sequence encoding Sprr1A, and a post-transcriptional regulatory sequence (PRE) flanked by AAV ITRs, can be constructed by directly inserting the nucleotide sequence of interest and the PRE into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al., Molecular & Cellular Biology, 8:3988-96 (1988); Vincent et al., Vaccines 90 (Cold Spring Harbor Laboratory Press, 1990); Carter, Current Opinion Biotechnology, 3:533-39 (1992); Muzyczka, Current Topics Microbiology & Immunology, 158:97-29 (1992); Kotin, Human Gene Therapy, 5:793-01(1994); Shelling et al., Gene Therapy, 1:165-69 (1994); and Zhou et al., J Experimental Medicine, 179:1867-75 (1994)). Alternatively, AAV ITRs can be excised from the viral genome or from an AAV vector containing the same and fused 5' and 3' of a selected nucleic acid construct that is present in another vector using standard ligation techniques, such as those described in Green & Sambrook (Green & Sambrook, *Molecular Cloning: A Laboratory Manual*, (4th ed., 2012)). Several AAV vectors are available from the American Type Culture Collection ("ATCC") under Accession Numbers 53222, 53223, 53224, 53225 and 53226.

In order to produce recombinant AAV particles, an AAV vector can be introduced into a suitable host cell using known techniques, such as by transfection. A number of transfection techniques are generally known in the art (See, e.g., Graham et al., Virology, 52:456 (1973); Green & Sambrook, *Molecular Cloning: A Laboratory Manual*, (4th ed., 2012); Davis et al., Basic Methods Molecular Biology, (Elsevier, 1986); and Chu et al., Gene, 13:197 (1981)). Particularly suitable transfection methods include calcium phosphate co-precipitation (Graham et al., Virology, 52:456-67 (1973)), direct microinjection into cultured cells (Capecchi, Cell, 22:479-88 (1980)), electroporation (Shigekawa et al., BioTechniques, 6:742-51 (1988)), liposome mediated gene transfer (Mannino et al., BioTechniques, 6:682-90 (1988)), lipid-mediated transduction (Feigner et al., Proceedings Nat'l Acad. Sci. USA, 84:7413-17(1987)), and nucleic acid delivery using high-velocity microprojectiles (Klein et al., Nature 327:70-73 (1987)).

Suitable host cells for producing recombinant AAV particles include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed. Non-limiting examples include CHO DHFR-minus cells (Urlaub and Chasin Proceedings Nat'l Acad. Sci. USA, 77:4216-420 (1980)), 293 cells (Graham et al., J. General Virology 36:59-72 (1977)), or myeloma cells like SP2 or NSO (Galfre & Milstein, Methods Enzymology, 73:3-46 (1981)).

In one embodiment, cells from the stable human cell line, 293 (readily available through, e.g., the ATCC under Accession No. ATCC CRL 1573). Particularly, the human cell line 293, which is a human embryonic kidney cell line that has been transformed with adenovirus type-5 DNA fragments (Graham et al., J. General Virology, 36:59-72 (1977)), and expresses the adenoviral E1a and E1b genes (Aiello et al., Virology, 94:460-69 (1979)). The 293 cell line is readily transfected, and provides a particularly convenient platform in which to produce AAV virions.

Host cells containing the above-described AAV vectors must be rendered capable of providing AAV helper functions in order to replicate and encapsidate the expression cassette flanked by the AAV ITRs to produce recombinant AAV particles. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV open reading frames (ORFs), namely the rep and cap coding regions, or functional homologues thereof.

The AAV rep coding region of the AAV genome encodes the replication proteins Rep 78, Rep 68, Rep 52, and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome. The AAV cap coding region of the AAV genome encodes the capsid proteins VP1, VP2, and VP3, or functional homologues thereof. AAV helper functions can be introduced into the host cell by transfecting the host cell with an AAV helper construct either prior to, or concurrently with, the transfection of the AAV vector comprising the expression cassette, AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products (See, e.g., Samulski et al., J. Virology, 63:3822-28 (1989); McCarty et al., J. Virology, 65:2936-45 (1991)). A number of other vectors have been described which encode Rep and/or Cap expression products (See. e.g., U.S. Pat. No. 5,139,941, incorporated by reference).

As a consequence of the infection of the host cell with a helper virus, the AAV Rep and/or Cap proteins are produced. The Rep proteins also serve to duplicate the AAV genome. The expressed Cap proteins assemble into capsids, and the AAV genome is packaged into the capsids. This results the AAV being packaged into recombinant AAV particles comprising the expression cassette. Following recombinant AAV replication, recombinant AAV particles can be purified from the host cell using a variety of conventional purification methods, such as CsCl gradients. The resulting recombinant AAV particles are then ready for use for gene delivery to various cell types.

In one embodiment, the number of viral vector and/or virion particles administered to a mammal may be on the order ranging from $10^3$ to $10^{15}$ particles/ml, or any values therebetween, such as for example, about $10^7$, $10^8$, $10^9$, $10^{10}$, $10^{11}$, $10^{12}$, $10^{13}$, $10^{14}$, or $10^{15}$ particles/ml. In one embodiment, vector and/or virion particles of higher than $10^{13}$ particles/ml are administered. Volumes between 1 µl and 10 ml may be administered such that the subject receives between $10^2$ and $10^{16}$ total vector and/or virion particles. Thus, in some embodiments, about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$ vector and/or virion particles are administered.

In certain instances, the AAV serotype is selected from AAV1, AAV2, AAV3, AAV4, AAV5, AAV6, AAV6.2, AAV7, AAV8, AAV9, rh.10, rh.39, rh.43, and CSp3.

Alternatively, a vector of the invention can be a virus other than the adeno-associated virus, or portion thereof, which allows for expression of a nucleic acid molecule introduced into the viral nucleic acid. For example, replication defective retroviruses, adenoviruses, herpes simplex viruses, and lentivirus can be used. Protocols for producing recombinant retroviruses and for infecting cells in vitro or in vivo with such viruses can be found in Ausubel et al., Current Protocols in Molecular Biology §§ 9.10-9.14 (Greene Publishing Associates, 1989) and other standard laboratory manuals. Examples of suitable retroviruses include pLJ, pZIP, pWE and pEM, which are well known to those skilled in the art. Examples of suitable packaging virus lines include Crip, Cre, 2 and Am. The genome of adenovirus can be manipulated such that it encodes and expresses the protein of interest but is inactivated in terms of its ability to replicate in a normal lytic viral life cycle (See e.g., Berkner et al., BioTechniques, 6:616-29 (1988); Rosenfeld et al., Science, 252:431-34 (1991); Rosenfeld et al., Cell 68:143-55 (1992)). Suitable adenoviral vectors derived from the adenovirus strain Ad type 5 d1324 or other strains of adenovirus (e.g., Ad2, Ad3, Ad7 etc.) are well known to those skilled in the art.

2. Lentivirus

Lentiviral vectors may be utilized to express genes in the nervous system, and the production of suitable lentiviral vectors is well known in the art (See, e.g., U.S. patent application Ser. No. 13/893,920, incorporated by reference). The lentiviral vector according to the present invention may be derived from or may be derivable from any suitable lentivirus. A recombinant lentiviral particle is capable of transducing a target cell with a nucleotide of interest. Once within the cell the RNA genome from, the vector particle is reverse transcribed into DNA and integrated into the genome of the target cell.

Lentiviral vectors are part of a larger group of retroviral vectors. A detailed list of lentiviruses may be found in Coffin et al., Retroviruses 758-763 (Cold Spring Harbor Laboratory Press, 1997). In brief, lentiviruses can be divided into primate and non-primate groups. Examples of primate lentiviruses include but are not limited to the human immunodeficiency virus (HIV) and the simian immunodeficiency virus (SrV). The non-primate lentiviral group includes the prototype "slow virus" visnaimaedi virus (VMV), as well as the related caprine arthritis-encephalitis virus (CAEV), equine infectious anemia virus (EIAV), feline immunodeficiency virus (FIV), bovine immunodeficiency virus (BIV).

Lentiviruses differ from other members of the retrovirus family in that lentiviruses have the capability to infect both dividing and non-dividing cells (Lewis et al., EMBO J., 11:3053-58 (1992)); Lewis & Emerman, J Virology, 68:510-16 (1994)). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. That component part may be involved in the biological mechanisms by which the vector infects cells, expresses genes or is replicated. The basic structure of retrovirus and lentivirus genomes share many common features such as a 5' LTR and a 3' LTR, between or within which are located a packaging signal to enable the genome to be packaged, a primer binding site, integration sites to enable integration into a host cell genome and gag, pol and env genes encoding the packaging components, which are polypeptides required for the assembly of viral particles. Lentiviruses have additional features, such as the rev and rev response element (RRE) sequences, which enable the efficient export of RNA transcripts of the integrated provirus from the nucleus to the cytoplasm of an infected target cell. In the provirus, the viral genes are flanked at both ends by regions called long terminal repeats (LTRs). The LTRs are responsible for proviral integration, and transcription. LTRs also serve as enhancer-promoter sequences and can control the expression of the viral genes. The LTRs themselves are identical sequences that can be divided into three elements, which are called "U3," "R" and "U5." U3 is derived from the sequence unique to the 3' end of the RNA, R is derived from a sequence repeated at both ends of the RNA, and U5 is derived from the sequence unique to the 5' end of the RNA. The sizes of the three elements can vary considerably among different viruses.

In a defective lentiviral vector genome gag, pol and env may be absent or non-functional. The R regions at both ends of the RNA are repeated sequences. U5 and U3 represent unique sequences at the 5' and 3' ends of the RNA genome respectively.

In a typical lentiviral vector of the present invention, at least part of one or more protein coding regions essential for replication may be removed from the virus, which makes the viral vector replication-defective. Portions of the viral genome may also be replaced by a nucleic acid in order to generate a vector comprising the nucleic acid which is capable of transducing a target non-dividing host cell and/or integrating its genome into a host genome. In one embodiment, the lentiviral vectors are non-integrating vectors as described in U.S. patent application Ser. No. 12/138,993 (herein incorporated by reference).

In a further embodiment, the vectors have the ability to deliver a sequence which is devoid of or lacking viral RNA. A heterologous binding domain (heterologous to gag) may be located on the RNA to be delivered and a cognate binding domain on gag or pol can be used to ensure packaging of the RNA to be delivered. Both of these vectors are described in U.S. patent application Ser. No. 12/139,035 (herein incorporated by reference). The lentiviral vector may be a "non-primate" vector, i.e., derived from a virus which does not primarily infect primates, especially humans.

The examples of non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi-visna virus (MV) or an equine infectious anemia virus (EIAV).

In some embodiments, the viral vector is derived from EIAV. EIAV has the simplest genomic structure of the lentiviruses. In addition to the gag, pol and env genes, EIAV encodes three other genes: tat, rev, and S2. Tat acts as a transcriptional activator of the viral LTR (Derse & Newbold, Virology, 194:530-36(1993); Maury et al., Virology, 200: 632-42(1994)). Rev regulates and coordinates the expression of viral genes through rev-response elements (RRE) (Martarano et al., J. Virology, 68:3102-11 (1994)). The mechanisms of action of these two proteins are thought to be broadly similar to the analogous mechanisms in the primate viruses (Martarano et al., J. Virology, 68:3102-11 (1994)). The function of S2 is unknown. In addition, an EIAV protein, Ttm, has been identified that is encoded by the first exon of tat spliced to the env coding sequence at the start of the transmembrane protein.

The viral vector may be manipulated to remove the non-essential elements and to retain the essential elements in order to provide the required functionality to infect, transduce and deliver a nucleotide sequence of interest to a target host cell (See, e.g., U.S. Pat. No. 6,669,936, incorporated by reference). In some embodiments, the genome is limited to sufficient lentiviral genetic information to allow packaging of an RNA genome, in the presence of packaging components, into a viral particle capable of infecting a target cell. Infection of the target cell may include reverse transcription and integration into the target cell genome. The lentiviral vector carries non-viral coding sequences which are to be delivered by the vector to the target cell. In some embodiments, the vector is incapable of independent replication to produce infectious lentiviral particles within the final target cell. Usually the recombinant lentiviral vector lacks a functional gag-pol and/or env gene and/or other genes essential for replication. The vector of the present invention may be configured as a split-intron vector (See, e.g., U.S. Pat. No. 7,303,910, incorporated by reference).

The vector may be a self-inactivating vector. Self-inactivating retroviral vectors may be constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al., Proceedings Nat'l Acad. Sci. USA, 83:3194-98 (1986); Dougherty and Temin et al., Proceedings Nat'l Acad. Sci. USA, 84:1197-01 (1987); Hawley, Proceedings Nat'l Acad. Sci. USA, 84:2406-10 (1987); Yee et al., Proceedings Nat'l Acad. Sci. USA, 91:9564-68 (1994)). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al., Nucleic Acids Research, 11:1855-72 (1983)) or suppression of transcription (Emerman & Temin, Cell, 39:449-67 (1984)). This strategy can also be used to eliminate downstream transcription from the 3' LTR into genomic DNA (Herman & Coffin, Science, 236:845-48 (1987)). This is of particular concern in human gene therapy where it is of critical importance to prevent the adventitious activation of an endogenous oncogene.

The plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed lentiviral sequence, i.e. the 5' U3 region, or they may be a heterologous promoter such as another viral promoter, for example the CMV promoter. Some lentiviral genomes require additional sequences for efficient virus production. For example, in the case of HIV, the rev and RRE sequences are preferably included; however the requirement for rev and RRE may be reduced or eliminated by codon optimization (See U.S. patent application Ser. No. 12/587,236, incorporated by reference). Alternative sequences which perform the same function, as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, the Rex protein of HTLV-1 can functionally replace the Rev protein of HIV-1. It is also known that Rev and Rex have similar effects to IRE-BP.

In a particular embodiment, the lentiviral vector according to the present invention consists of a self-inactivating minimal lentiviral vector, derived from Equine Infectious Anemia Virus (EIAV), encoding a gene for Sprr1A. The vector may be produced by the transient transfection of cells (e.g. HEK293T cells) with three plasmids, encoding for: (1) the recombinant EIAV ProSavin® (Oxford BioMedica plc, Oxford UK) vector genome (Farley et al., J. Gen. Med., 9:345-56 (2007); U.S. Pat. No. 7,259,015, incorporated by reference); (2) the synthetic EIAV gag/pol expression vector (pESGPK, U.S. patent application Ser. Nos. 13/893,920 and 12/587,236, incorporated by reference) and (3) the VSV-G envelope expression vector (pHGK).

3. Herpes Simplex Virus

Herpes simplex virus (HSV) vectors may also be utilized to express a gene in the nervous system. The genome of the type-1 (HSV-1) is about 150 kb of linear, double-stranded DNA, featuring about 70 genes. Many viral genes may be deleted without the virus losing its ability to propagate. The "immediately early" (IE) genes are transcribed first. They encode trans-acting factors which regulate expression of other viral genes. The "early" (E) gene products participate in replication of viral DNA. The late genes encode the structural components of the virion as well as proteins that turn on transcription of the IE and E genes or disrupt host cell protein translation.

The HSV vector may be a plasmid-based system, whereby a plasmid vector (termed an amplicon) is generated that contains a nucleotide sequence encoding the gene and two cis-acting HSV recognition signals. The recognition signals are the origin of DNA replication and the cleavage packaging signal, which encode no HSV gene products. Thus, helper virus is required to replicate the amplicon and package it into an HSV coat. The vector therefore expresses no viral gene products within the recipient cell, and recombination with or reactivation of latent viruses by the vector is limited due to the minimal amount of HSV DNA sequence present within the defective HSV vector genome.

Examples of HSV-mediated gene therapy are well known in the art (Breakefield & DeLuca. New Biologist, 3:203-18 (1991); Ho & Mocarski, Virology, 167:279-93 (1988); Palella, et al., Molecular & Cellular Biology, 8:457-60 (1988); Palella et al., Gene, 80:137-44 (1988); Andersen et al., Human Gene Therapy, 3:487-99 (1992); Kaplitt et al., Current Topics Neuroendocrinology, 11:169-91 (1993); Spade & Frenkel, Cell, 30:295-04 (1982); Kaplitt et al., Molecular & Cellular Neuroscience, 2:320-30 (1991); Federoff et al., Proceedings Nat. Acad. Sci. USA, 89:1636-40 (1992)).

4. Adenovirus

Adenovirus vectors may be utilized to express genes in the nervous system. The adenovirus genome consists of about 36 kb of double-stranded DNA. Adenoviruses target airway epithelial cells, but are also capable of infecting neurons. Recombinant adenovirus vectors have been used as gene transfer vehicles for non-dividing cells. These vectors are similar to recombinant HSV vectors, since the adenovirus E1a immediate-early gene is removed but most viral genes are retained. Since the E1a gene is small (roughly 1.5 kb) and the adenovirus genome is approximately one-third of the size of the HSV genome, other non-essential adenovirus genes are removed in order to insert a foreign gene within the adenovirus genome.

Examples of adenovirus-mediated gene therapy are well known in the art (Akli et al., Nature Genetics, 3:224-28 (1993); La Salle et al., Science, 259:988-90 (1993), La Salle, Nature Genetics, 3:1-2 (1993); Neve, Trends Biochemical Sci., 16:251-53 (1993)).

C. Non-Viral Vectors

Sprr1A can be delivered using a non-viral delivery system, for example, as naked nucleic acid, in combination with a delivery reagent. Any nucleic acid delivery method known in the art can be used in the methods described herein. This includes delivery of a nucleic acid to the desired tissues in colloidal dispersion systems that include, for example, macromolecule complexes, nanocapsules, microspheres, beads, and lipid-based systems including oil-in-water emulsions, micelles, mixed micelles, and liposomes. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Research, 32:e109 (2004); Hanai et al. Annals N.Y. Acad. Sci., 1082:9-17 (2006); Kawata et al. Molecular Cancer Therapeutics, 7:2904-12 (2008).

Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., BioTechniques, 6:682-90 (1988)).

Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. Examples of suitable lipids liposomes production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3β-[N—(N',N'-dimethylaminoethane) carbamoyl] cholesterol. A variety of methods are known for preparing liposomes, for example, as described in Szoka et al., Annual Rev. Biophysics & Bioengineering, 9:467-08 (1980); and U.S. Pat. Nos. 4,235,871; 4,501,728; 4,837,028; and 5,019,369, which are herein incorporated by reference.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 angstroms, containing an aqueous solution in the core.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

D. Pharmaceutical Formulations

Formulations of pharmaceutically-acceptable excipients and carrier solutions are well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual subject.

Sterile injectable solutions are prepared by incorporating the virus, nucleic acid, or other vector in the required amount in the appropriate solvent with various of the other ingredients enumerated herein and known to those skilled in the art, as required, followed by filtered sterilization. Generally, dispersions are prepared by incorporating the various sterilized active ingredients into a sterile vehicle which contains the basic dispersion medium and the required other ingredients from those enumerated herein. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may also be formulated in a neutral or salt form. Pharmaceutically-acceptable salts, include the acid addition salts (formed with the free amino groups of the AAV capsid) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

Carriers include any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

Delivery vehicles such as liposomes, nanocapsules, microparticles, microspheres, lipid particles, vesicles, and the like, may be used for the introduction of the compositions of the present invention into suitable host cells. In particular, nucleic acids may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the AAV constructs disclosed herein. The formation and use of liposomes is generally known to those of skill in the art. Recently, liposomes were developed with improved serum stability and circulation half-times (U.S. Pat. No. 5,741,516, incorporated by reference). Further, various methods of liposome and liposome like preparations as potential drug carriers have been described (U.S. Pat. Nos. 5,567,434; 5,552,157; 5,565,213; 5,738,868 and 5,795,587, incorporated by reference).

Alternatively, nanocapsule formulations of the AAV vector may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

E. Administration of the Composition

In one embodiment of the invention, the viral and nucleic acid vectors will be formulated into pharmaceutical compositions and administered by injection directly into the brain. If desired, an Omaya reservoir can be placed within the surgical site to enable repeat administration of a composition.

Precise delivery of a composition into the substantia nigra can be conducted using stereotactic microinjection techniques. For example, the subject being treated can be placed within a MRI-compatible stereotactic frame base and then imaged using high resolution MRI to determine the three-dimensional positioning for the particular injection. The MRI images are then transferred to a computer having the appropriate stereotactic software, and a number of images are used to determine a target site and trajectory for a microinjection. The software translates the trajectory into three-dimensional coordinates that are appropriate for the stereotactic frame. In the case of intracranial delivery, the skull will be exposed, burr holes will be drilled above the entry site, and the stereotactic apparatus positioned with the needle implanted at a predetermined depth. A pharmaceutical composition comprising a viral or nucleic acid vector can then be microinjected at the selected target sites. In some embodiments, the composition is injected by an osmotic pump or an infusion pump, such as a convection-enhanced delivery device. The spread of the vector from the site of injection will be a function of diffusion, which may be controlled by adjusting the concentration of the vector in the pharmaceutical composition In some embodiments, the composition is injected during the implantation of a brain pacemaker for deep brain stimulation. In other embodiments, the composition is injected during a pallidotomy.

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXEMPLIFICATION

Example 1. Dopamine Producing Neurons of the Substantia Nigra Upregulate Sprr1A in a Rat Model of Parkinson's Disease To address the problem of early axonal degeneration in Parkinson's Disease, the progressive gene expression changes in the rat ventral midbrain were monitored from an intrastriatal 6-hydroxydopamine (OHDA) lesion over 16 weeks. The patterns of gene expression within the substantia nigra (SN) characterized by early, highly-upregulated expression may be indicative of potential protective responses to a striatal 6-OHDA insult. The largest grouping of genes fitting this expression pattern was in the regeneration-associated gene (RAG) family. The most highly upregulated RAG was Sprr1A (FIG. 1), which has been shown to facilitate post-injury axonal regeneration in peripheral nerves through stabilizing the cytoskeleton at the growth cone. Sprr1A upregulation was confirmed using RNA scope in situ hybridization in degenerating substantia nigra dopamine (tyrosine hydroxylase immunohistochemistry) neurons.

Figure 2:
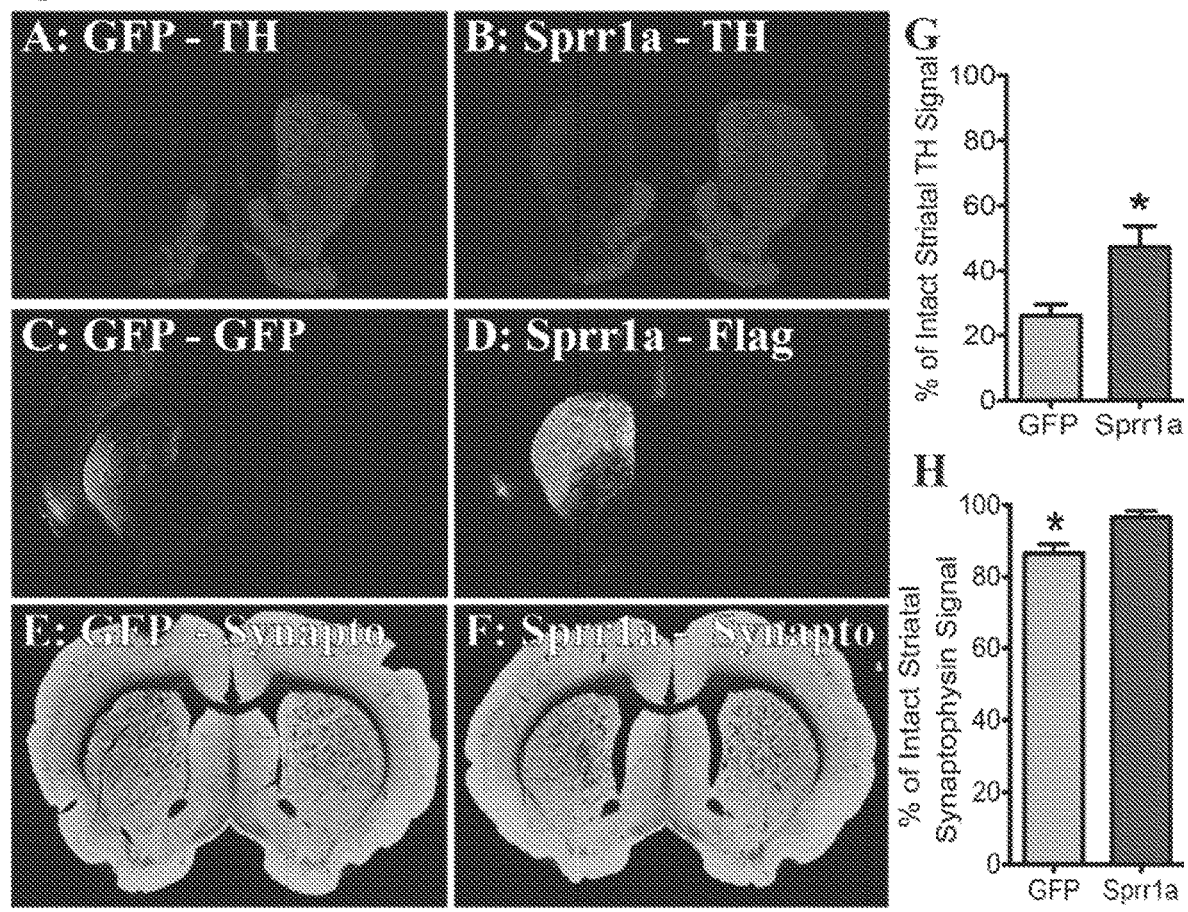
FIG. 2 consists of eight panels, labelled panels A-H.
Figure 3:
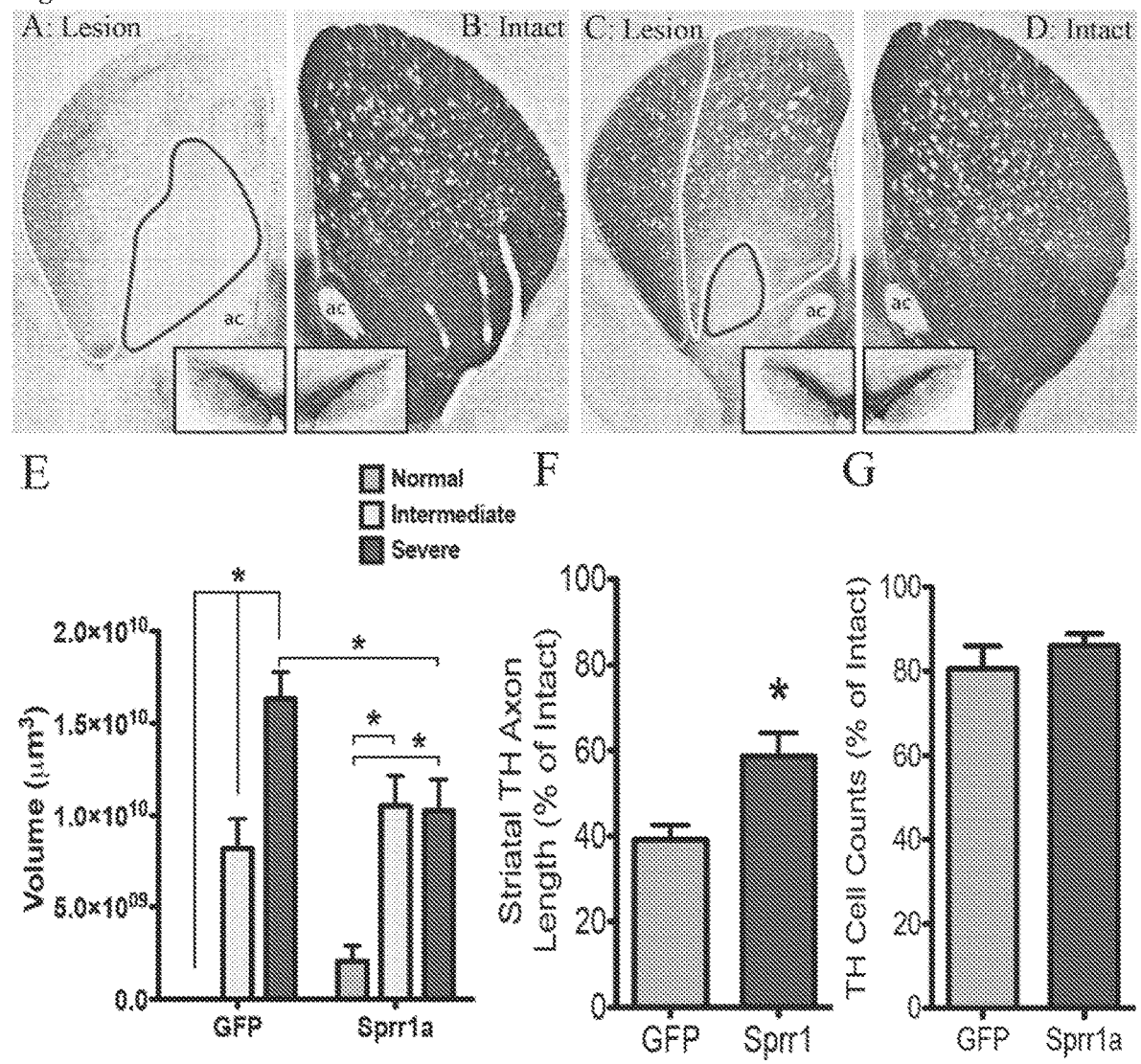
FIG. 3 consists of seven panels, labelled panels A-G.

Example 2. Increasing the Expression of Sprr1A Protects Dopamine Neurons from Denervation Sprr1A or control green fluorescent protein (GFP) was overexpressed with AAV constructs in the substantia nigra followed 1 month later with a striatal 6-OHDA lesion. Animals receiving AAV-Sprr1A exhibited significant protection of nigrostriatal axons in the striatum as compared to AAV-GFP as measured by tyrosine hydroxylase densitometry (FIG. 2). The protective effect of Sprr1A was further confirmed by both stereological measurements of tyrosine hydroxylase fiber density and volumetric assessments of striatal zones exhibiting severe, intermediate, or no lesion (FIG. 3). Animals treated with AAV-Sprr1A had significantly higher tyrosine hydroxylase-positive axon density in the striatum and significantly smaller zones of severe denervation as compared to GFP controls (FIG. 3). AAV-Sprr1a treatment prohibited significant synapse loss (a measure of overt axonal degeneration) in the lesioned striatum, as indicated by levels of striatal synaptophysin (a synaptic marker) (FIG. 2). Finally. Sprr1a overexpression in an intact (i.e. unlesioned) nigrostriatal system does not produce overt neurotoxicity of axonal degeneration (FIG. 4). These data show that Sprr1A is part of the dopamine neuron's natural armamentarium to resist axonal degeneration and that it can be safely augmented to mitigate the loss of striatal dopaminergic fibers in a rat 6-OHDA model.

Example 3: Experimental Methods

Preparation of the Vector:

The Sprr1A protein is expressed via the use of an AAV vector. A nucleotide sequence encoding Sprr1A is cloned and inserted into an AAV plasmid backbone (AAV-Sprr1A), and the gene for green fluorescent protein (GFP) is cloned and inserted into a different AAV plasmid backbone as a control (AAV-GFP). The expression of the transgene is driven by the chicken beta actin/cytomegalovirus enhancer (CβA/CMV). Vectors containing AAV2 ITRs are packaged into AAV5 capsids via co-transfection with a plasmid containing the AAV rep and cap genes and adenovirus helper functions. Particles are purified using iodixanol gradients and 1-sepharose chromatography, and dot blot is used to determine vector titers. Viral preparations are stored at 4'C and kept on wet ice during surgical procedures. All pipette, syringe, and centrifuge tube surfaces are coated with SigmaCote (Sigma-Aldrich, St. Louis, Mo.) prior to coming in contact with virus to minimize the binding of viral particles.

6-OHDA Rat Parkinson's Disease Model:

Adult male Sprague-Dawley rats are rendered parkinsonian using 6-hydroxydopamine according to the procedure detailed in Spieles-Engemann, A. L., M. M. Behbehani, T. J. Collier, S. L. Wohlgenant, K. Steece-Collier, K. Paumier, B. F. Daley, S. Gombash, L. Madhavan, G. T. Mandybur, J. W. Lipton, B. T. Terpstra, and C. E. Sortwell, *Stimulation of the rat suhbthalamic nucleus is neuroprotective following significant nigral dopamine neuron loss*. Neurobiology of Disease, 2010, 39(1):105-15.

Delivery of Vector to the Substantia Nigra:

Sprague Dawley rats are unilaterally injected in the substantia nigra with $10^{12}$ to $10^{14}$ recombinant viral particles. First, rats are anesthetized with 5% isofluorane in oxygen for induction and 2% isofluorane in oxygen for maintenance. Rats are placed in a stereotaxic frame and two 2 µl injections of either AAV-Sprr1A or AAV-GFP are injected into the substantia nigra using a Hamilton syringe fitted with a glass capillary needle (Hamilton Gas Tight syringe 80,000, 26 s/2" needle; Hamilton. Reno, Nev.; coated with SigmaCote). The vector injection begins immediately after the needle is lowered to the site. Vector is injected at a rate of 0.05-0.50 µl/minute, and the needle remains in place after the injection for an additional five minutes before retraction.

Example 4: Increasing the Expression of Sprr1A in a Monkey Model

Non-Human Primate Parkinson's Disease Model:

Rhesus monkeys are excellent models for studying Parkinson's Disease based on the evolution of their parkinsonian symptoms. Animals are lesioned by infusing 2.5-3.5 mg of 1-methyl-4-phenyl-1,2,3,6-tetrahydropyridine HCL (MPTP-HCL) through the right internal carotid artery (referred to as ipsilateral side) followed by 4 I.V. doses of 0.3 mg/kg of MPTP-HCL (referred to as contralateral side) until a stable, overlesioned hemi-parkinsonian syndrome is achieved (Eberling, Brain Research, 805:259-62 (1998)). The primate MPTP model is the gold standard model of evaluation prior to human trials (Langston, Trends Pharmacological Sci., 6:375-78 (1985)). MPTP is converted in the CNS to 1-methyl-4-phenylpyridinium (MPP+) by monoamine oxidase B. MPP+ is a potent neurotoxin which causes degeneration of the nigral dopaminergic neurons and loss of the nigro-striatal dopamine pathway, as seen in Parkinson's disease.

Delivery of Vector to the Substantia Nigra:

In the surgery room, a sterile field is created to prepare the infusion system. Infusion cannulae are flushed with saline to assess the integrity between the needle and tubing interface. Sterile infusion cannulae and loading lines are connected using the appropriate fittings with extreme caution taken to prevent the collection of air bubbles in the system. Non-sterile oil infusion lines are prepared and 1 ml gas tight Hamilton syringes filled with oil are attached to an infusion pump. Six infusion cannulae are fitted onto microdialysis holders (3 cannulae per holder) and mounted onto a stereotactic tower. Following the union of the oil and loading lines, the needle cannulae are primed with AAV and the infusion system is transferred to the surgery table. Initial infusion rates are set at 0.1 pl/minute, the lines are visually inspected to ensure a smooth flow of fluid through the system, and the cannulae are manually lowered to their target sites. A final visual inspection is performed to check for any air bubbles in the infusion system.

The cannula system consists of three components: (i) a sterile infusion cannula; (ii) a sterile loading line housing AAV-Sprr1A or AAV-GFP; and (iii) a non-sterile infusion line containing oil. The infusion cannula consists of 27 G needles (outer diameter, 0.03"; inner diameter, 0.06") fitted with fused silica (outer diameter, 0.016", inner diameter, 0.008"), and placed in Teflon tubing (0.03" ID) such that the distal tip of the silica extends approximately 15 mm out of the tubing. The needle is secured into the tubing using superglue and the system is checked for leaks prior to use. At the proximal end of the tubing, a Tefzel fitting and ferrule are attached to connect the adjacent loading line.

Loading and infusion lines consist of 50 cm sections of Teflon tubing (outer diameter, 0.062"; inner diameter, 0.03") fitted with Tefzel 1/16" ferrules, unions, and male Luer-lock adapters at the distal ends. The sterile loading lines accommodate up to a 1000 ml volume, and they are primed with saline prior to use.

The animals are initially sedated with Ketamine (10 mg/kg, i.m.), intubated, and prepped for surgery. A venous line is established using a 22 gauge catheter positioned in the cephalic or saphenous vein to deliver isotonic fluids at 5-10 ml/kg/hr. Isoflurane is delivered at 1-3% until the animal maintained a stable plane of anesthesia. The head is placed in an MRI compatible stereotactic frame according to pre-set values attained during a baseline MRI scan. The animal is instrumented with subcutaneous electrocardiogram electrodes and a rectal probe, and the body is covered with circulating water blankets to maintain a core temperature of 36-38° C. Electrocardiogram, heart rate, and body temperature are continuously monitored during the procedure. The head is prepped with Betadine and 70% ethanol, a sterile field is created, and a midline incision is performed through the skin, muscle, and fascia using electrocautery.

Gentle retraction of fascia and muscle allows for cranial exposure over cortical entry sites. A unilateral craniotomy is performed using a drill to expose a 3 cm×2 cm area of dura mater above the target sites. Multiple needle cannulae attached to a holder are stereotactically guided to striatal target sites. Surgical parameters for the unilateral infusion of AAV into the hemisphere ipsilateral to ICA MPTP infusion are summarized in Table 1.

TABLE I

| Infusion parameters | |
|---|---|
| Infusion Volume | 30 µl per site |
| Infusion Rates | 0.1 µl/min (60 min) |
| | 0.2 µl/min (60 min) |
| | 0.4 µl/min (30 min) |
| Virus | AAV-Sprr1A; $1 \times 10^{12}$ particles/ml |
| Control | AAV-GFP; $1 \times 10^{12}$ particles/ml |

Approximately fifteen minutes following infusion, the cannulae assembly is raised at a rate of 1 mm/minute until it is out of the cortex. The cortex is rinsed with saline, the bone margins are trimmed with ronguers, and the wound site is closed in anatomical layers. Analgesics (Numorphan, 1M) and antibiotics (Flocillin, 1M) are administered as part of the surgical protocol. Animals are monitored for full recovery from anesthesia, placed in their home cages, and clinically observed for several days following surgery.

Example 5: Increasing Sprr1A Activity in Human Subjects

Human patients are bilaterally infused with a total dose of $10^{10}$ to $10^{15}$ AAV-Sprr1A particles per subject in 100-1000 µL total volume. AAV-Sprr1A is administered to the substantia nigra by intrastriatal infusion delivered by means of a stereotactically positioned cannula. The administration device includes a surgical stainless steel cannula with a stepped design to facilitate convection enhanced delivery, biocompatible Teflon tubing, and a syringe. The device is attached to a syringe pump to achieve a consistent rate of infusion of 1 µL per minute.

Post-surgical visits occur at 1, 2 and 4 weeks post-surgery. The visits at weeks 1 and 2 primarily involve post-surgical care, e.g. dressing change. Subjects are followed for a total of 6 months, with examinations occurring at 1-month intervals until the third month. Behavioral assessments will occur at baseline, three and six months.

INCORPORATION BY REFERENCE

All of the patents, published patent applications, and non-patent literature cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating Parkinson's Disease in a subject in need thereof, comprising administering to the subject a therapeutically effective amount of a composition comprising a nucleic acid molecule that encodes a Sprr1A protein, or a biologically-active portion thereof, wherein said nucleic acid molecule comprises at least 90% sequence homology to the nucleotide sequence set forth in SEQ ID NO:1, and wherein said composition increases the activity of a small proline-rich repeat 1a protein ("Sprr1A"), and wherein the composition is delivered to the brain.

2. The method of claim 1, wherein said composition comprises a virus.

3. The method of claim 2, wherein the virus is an adeno-associated virus ("AAV"), adenovirus, herpes simplex virus, or lentivirus.

4. The method of claim 3, wherein the virus is AAV.

5. The method of claim 4, wherein the virus is AAV1.

6. The method of claim 2, wherein the genome of said virus comprises said nucleic acid molecule.

7. The method of claim 1, wherein said nucleic acid molecule comprises a nucleotide sequence that has at least 95% sequence homology with the nucleotide sequence set forth in SEQ ID NO:1.

8. The method of claim 1, wherein said nucleic acid molecule encodes an amino acid sequence that has at least 80% sequence homology with the amino acid sequence set forth in SEQ ID NO:2.

9. The method of claim 1, wherein said nucleic acid molecule encodes an amino acid sequence that has at least 95% sequence homology with the amino acid sequence set forth in SEQ ID NO:2.

10. The method of claim 1, wherein the composition is delivered to the substantia nigra, nigrostriatal system, hippocampus, medial temporal lobe, cerebral cortex, or spinal cord.

11. The method of claim 1, wherein delivering the composition comprises injecting the composition.

12. The method of claim 1, wherein the subject is a mammal.

13. The method of claim 12, wherein the subject is a primate, porcine, canine, ovine, or rodent.

14. The method of claim 12, wherein the subject is a human.

* * * * *

SEQUENCE LISTING

<160> NUMBER OF SEQ ID NOS: 5

<210> SEQ ID NO 1
<211> LENGTH: 267
<212> TYPE: DNA

<213> ORGANISM: Homo sapiens

<400> SEQUENCE: 1

```
atgaattctc agcagcagaa gcagccttgc accccacccc ctcagcctca gcagcagcag    60
gtgaaacaac cttgccagcc tccaccccag gaaccatgca tcccaaaaac caaggagccc   120
tgccacccca aggtgcctga gccctgccac cccaaagtgc ctgagccctg ccagcccaag   180
gttccagagc cctgccagcc caaggtgcct gagccctgcc cttcaacggt cactccagca   240
ccagcccagc agaagaccaa gcagaag                                       267
```

<210> SEQ ID NO 2
<211> LENGTH: 89
<212> TYPE: PRT
<213> ORGANISM: Homo sapiens

<400> SEQUENCE: 2

```
Met Asn Ser Gln Gln Gln Lys Gln Pro Cys Thr Pro Pro Gln Pro
1               5                   10                  15
Gln Gln Gln Gln Val Lys Gln Pro Cys Gln Pro Pro Gln Glu Pro
                20                  25                  30
Cys Ile Pro Lys Thr Lys Glu Pro Cys His Pro Lys Val Pro Glu Pro
            35                  40                  45
Cys His Pro Lys Val Pro Glu Pro Cys Gln Pro Lys Val Pro Glu Pro
        50                  55                  60
Cys Gln Pro Lys Val Pro Glu Pro Cys Pro Ser Thr Val Thr Pro Ala
65                  70                  75                  80
Pro Ala Gln Gln Lys Thr Lys Gln Lys
                85
```

<210> SEQ ID NO 3
<211> LENGTH: 812
<212> TYPE: DNA
<213> ORGANISM: Rattus sp.

<400> SEQUENCE: 3

```
ctgagagcct gctcttctct gagtattaga accaagtact acctaatcat gagttcccac    60
cagcagaagc agccttgcac tgtaccccct cagctgcacc agcagcaggt gaaacagcct   120
tgccagccac caccccagga accttgtgct cccaaaacta aggagccctg tcaccctatt   180
cctgagccct gcaaccccaa ggtgccagag ccctgccagc taaggtgcc agagccttgt   240
caacctaagg tgccagagcc ttgccagcct aaggtgccag agccttgcca gcctaaggtg   300
ccagagcctt gccagcctaa ggtgccagag ccctgccagc taaggtgcc agagccctgc   360
catcccaagg cacctgagcc ctgccaccct gttgttcccg agccctgcca gcctgttgct   420
cctgagccct gccagcctgt tgttcctgaa ccctgccccc aactgtcac tccatcacca   480
taccagcaga agacaaagca gaagtaatat tgtccatagc caagcctgaa gatctgatca   540
ccagatgctg aggctgcttt ccatcctgct tatgagtccc attgccttgt gctacacatg   600
ctgtgacctc cagtcttaat cctccatcct tgcaccacct aaaaagttgt ctctcatcct   660
catcctcaag agttctcgag ccactcaaca ttacccaaag tctcattgaa tggctaatct   720
ttccatggct caggattcat ctgaatgggg gtggggaata agacaagtat atgttcaata   780
ttcttcccct cattaaacac cttttaactc ca                                812
```

<210> SEQ ID NO 4
<211> LENGTH: 671

```
<212> TYPE: DNA
<213> ORGANISM: Homo sapiens

<400> SEQUENCE: 4
ccaagggacc acacagccca ttctgctccg tataccagct ttctgtctct agaaaaaaac    60
acatttgaag catgaattct cagcagcaga agcagccttg cacccaccc cctcagcctc    120 agcagcagca ggtgaaacaa ccttgccagc ctccacccca ggaaccatgc atccccaaaa   180
ccaaggagcc ctgccacccc aaggtgcctg agccctgcca ccccaaagtg cctgagccct   240
gccagcccaa ggttccagag ccctgccagc caaggtgcc tgagccctgc ccttcaacgg    300
tcactccagc accagcccag cagaagacca agcagaagta atgtggtcca cagccatgcc   360
cttgaggagc tggccactgg atactgaaca ccctactcca ttctgcttat gaatcccatt   420
tgcctattga ccctgcagtt agcatgctgt caccctgaat cataatcgct cctttgcacc   480
tctaaaaaga tgtcccttac cctcattctg gagggctcct gagcctctgc gtaaggctga    540
acgtctcact gactgagcta gtcttcttgt tgctcgggtg catttgagga tggatttggg    600
gaaggatcaa gtgaaccatc cctagtcttc cttcaataaa taacttttaa ctccaaaaaa    660 aaaaaaaaa a                                                        671

<210> SEQ ID NO 5
<211> LENGTH: 657
<212> TYPE: DNA
<213> ORGANISM: Homo sapiens

<400> SEQUENCE: 5
ccaagggacc acacagccca ttctgctccg tataccagaa aaaacacat ttgaagcatg     60 aattctcagc agcagaagca gccttgcacc ccaccccctc agcctcagca gcagcaggtg   120
aaacaacctt gccagcctcc accccaggaa ccatgcatcc caaaaccaa ggagccctgc    180 caccccaagg tgcctgagcc ctgccacccc aaagtgcctg agccctgcca gcccaaggtt   240
ccagagccct gccagcccaa ggtgcctgag ccctgccctt caacggtcac tccagcacca   300
gcccagcaga agaccaagca gaagtaatgt ggtccacagc catgcccttg aggagctggc   360
cactggatac tgaacaccct actccattct gcttatgaat cccatttgcc tattgaccct   420
gcagttagca tgctgtcacc ctgaatcata atcgctcctt tgcacctcta aaagatgtc    480 ccttaccctc attctggagg gctcctgagc ctctgcgtaa ggctgaacgt ctcactgact   540
gagctagtct tcttgttgct cgggtgcatt tgaggatgga tttggggaag gatcaagtga   600 accatccta gtcttccttc aataaataac ttttaactcc aaaaaaaaa aaaaaaa       657
```